United States Patent
Bradl et al.

(10) Patent No.: US 12,347,527 B2
(45) Date of Patent: Jul. 1, 2025

(54) DATA STORAGE DEVICE AND METHOD FOR STORING DATA USING AN OLIGONUCLEOTIDE NANOSTRUCTURE BACKBONE AND LABELS WITH DYES

(71) Applicant: LEICA MICROSYSTEMS CMS GMBH, Wetzlar (DE)

(72) Inventors: Joachim Bradl, Wetzlar (DE); Soeren Alsheimer, Wetzlar (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 0 days.

(21) Appl. No.: 18/452,615

(22) Filed: Aug. 21, 2023

(65) Prior Publication Data

US 2024/0071574 A1     Feb. 29, 2024

(30) Foreign Application Priority Data

Aug. 23, 2022   (EP) ..................... 22191690

(51) Int. Cl.
  *G16B 50/30*     (2019.01)
  *G06F 16/22*     (2019.01)
  *G06F 16/2455*   (2019.01)

(52) U.S. Cl.
  CPC ............ *G16B 50/30* (2019.02); *G06F 16/22* (2019.01); *G06F 16/24564* (2019.01)

(58) Field of Classification Search
  None
  See application file for complete search history.

(56) References Cited

U.S. PATENT DOCUMENTS 6,329,139 B1    12/2001  Nova et al.
2003/0228610 A1 * 12/2003  Seul ........................ C40B 60/14
                                                    435/287.2

(Continued)

FOREIGN PATENT DOCUMENTS

EP            4065729 B1 * 12/2023  ........ B01L 3/502761
WO    WO 2020/243187 A1    12/2020

(Continued)

OTHER PUBLICATIONS

Adam V, Mizuno H, Grichine A, Hotta JI, Yamagata Y, Moeyaert B, Nienhaus GU, Miyawaki A, Bourgeois D, Hofkens J. Data storage based on photochromic and photoconvertible fluorescent proteins. Journal of biotechnology. Sep. 15, 2010;149(4):289-98. (Year: 2010).*

(Continued)

*Primary Examiner* — Uyen T Le
(74) *Attorney, Agent, or Firm* — LEYDIG, VOIT & MAYER, LTD.

(57) ABSTRACT

A data storage device includes an oligonucleotide nanostructure backbone with a plurality of attachment sites at predetermined positions, a plurality of labels configured to attach to the attachment sites, and at least a first orientation indicator and a second orientation indicator. Each label includes at least one dye, and an attachment oligonucleotide portion configured to attach to one of the attachment sites. The attachment oligonucleotide portion of each label includes a unique oligonucleotide sequence configured to bind to a complementary sequence of one of the attachment sites.

11 Claims, 7 Drawing Sheets

(56) References Cited

U.S. PATENT DOCUMENTS

| | | | | |
|---|---|---|---|---|
| 2005/0147976 A1* | 7/2005 | Su | ........................ | C12Q 1/6874 |
| | | | | 435/6.12 |
| 2005/0272053 A1* | 12/2005 | Mao | ..................... | C12Q 1/6851 |
| | | | | 435/6.12 |
| 2010/0262374 A1* | 10/2010 | Hwang | ................... | B82Y 30/00 |
| | | | | 702/19 |
| 2014/0057805 A1 | 2/2014 | Wada et al. | | |
| 2018/0142286 A1 | 5/2018 | Dunaway et al. | | |
| 2020/0025752 A1 | 1/2020 | Gopinath et al. | | |
| 2021/0350879 A1* | 11/2021 | Perry | ................. | G11C 13/0019 |
| 2022/0042967 A1* | 2/2022 | Brown | ................ | G11C 13/0019 |

FOREIGN PATENT DOCUMENTS

| | | | | |
|---|---|---|---|---|
| WO | WO-2022103887 A1 * | 5/2022 | ............ | C12Q 1/6811 |
| WO | WO-2022104337 A1 * | 5/2022 | ......... | C12N 15/1068 |
| WO | WO 2022/242887 A1 | 11/2022 | | |

OTHER PUBLICATIONS

Mathur, Divita, et al. "Can a DNA origami structure constrain the position and orientation of an attached dye molecule?." The Journal of Physical Chemistry C 125.2 (2020): 1509-1522. (Year: 2000).*

Nguyen et al.: "Long-Term Stability and Integrity of Plasmid-Based DNA Data Storage,", *Polymers*, vol. 10, No. 1, Jan. 2018, pp. 1-10, MDPI, Switzerland.

Park et al.: "Macroscopic 10-Terabit-per-Square-Inch Arrays from Block Copolymers with Lateral Order," *Science*, vol. 323, No. 5917, pp. 1030-1033, Feb. 2009, US.

\* cited by examiner

DATA STORAGE DEVICE AND METHOD FOR STORING DATA USING AN OLIGONUCLEOTIDE NANOSTRUCTURE BACKBONE AND LABELS WITH DYES

CROSS REFERENCE TO RELATED APPLICATIONS

This application claims benefit to European Patent Application No. EP 22191690.1, filed on Aug. 23, 2022, which is hereby incorporated by reference herein.

FIELD

Embodiments of the present invention relate to a data storage device and a method for storing and accessing data.

BACKGROUND

DNA, a naturally occurring organic information storage molecule, is stable over hundreds to thousands of years due to its inherent chemical stability, even under unfavourable conditions. In the art, the use of DNA for direct writing of information into the DNA sequences and the stability of DNA written sequences has been established using accelerated aging tests performed at 65° C. for 20 days, which corresponds roughly to 20 years at −20° C. These tests found that the original message was maintained without errors (Long-Term Stability and Integrity of Plasmid-Based DNA Data Storage, by Nguyen et al., Polymers, Vol. 10, No. 1, January 2018).

Presently available commercially available data storage technologies allow densities in the range of 1-5 Tbit/inch$^2$. Experimental technologies have been shown that allow—10 Tbit/inch$^2$ corresponding to 125 G byte and 3 nm features using a bottom-up synthesis approach using block-copolymers (Macroscopic 10-Terabit-per-Square-Inch Arrays from Block Copolymers with Lateral Order, by Park et al., Science, Vol. 323, No. 5917, pp. 1030-1033, February 2009). However, with an increase in density the durability of storage media often decreases.

SUMMARY

Embodiments of the present invention provide a data storage device. The data storage device includes an oligonucleotide nanostructure backbone with a plurality of attachment sites at predetermined positions, a plurality of labels configured to attach to the attachment sites, and at least a first orientation indicator and a second orientation indicator. Each label includes at least one dye, and an attachment oligonucleotide portion configured to attach to one of the attachment sites. The attachment oligonucleotide portion of each label includes a unique oligonucleotide sequence configured to bind to a complementary sequence of one of the attachment sites.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
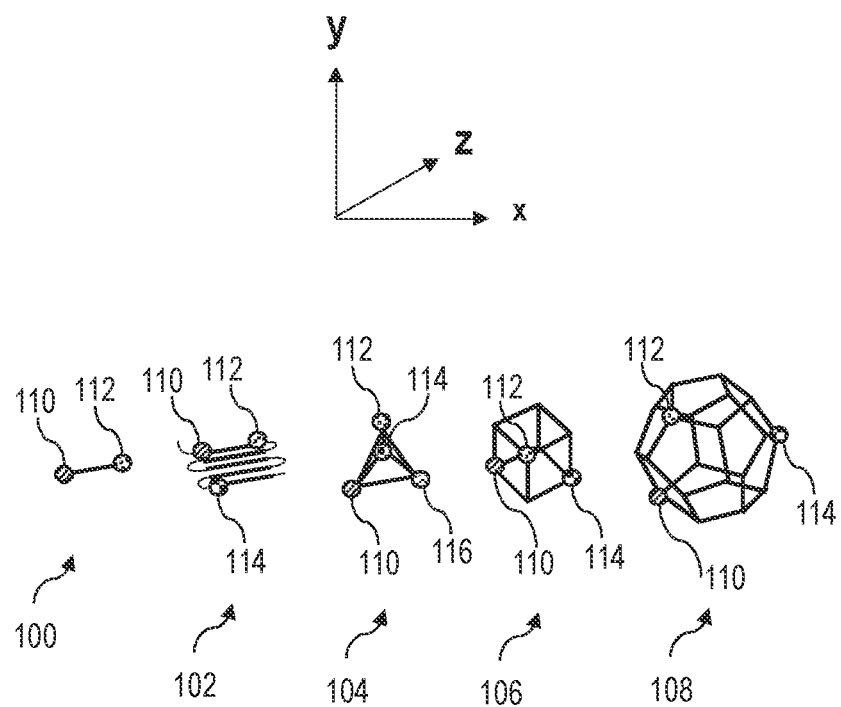
FIG. 1 shows several nanostructure backbones with orientation indicators according to some embodiments.

Embodiments of the present invention provide a data storage device and a method that enable high-density, long-term storage of data.

Recently, DNA origami technology has opened the possibility to design arbitrary nanostructures based on DNA scaffolds and DNA staple strands. These base structures can be used to place labels with nanometer precision in 3D using position-specific staple strands, which may be connected either directly or indirectly to a label. Embodiments of the present invention take advantage of these disparate technologies to solve the problem of high-density long-term—preferably encrypted—data storage based on widely available and inexpensive substrates.

In one aspect an organic data storage device is provided, comprising: an oligonucleotide nanostructure backbone with a plurality of attachment sites at predetermined positions; a plurality of labels configured to attach to some or all of the attachment sites; at least a first orientation indicator and a second orientation indicator; wherein each label comprises at least one dye, and an attachment oligonucleotide portion configured to attach the label to one of the attachment sites; and wherein the attachment oligonucleotide portion of each label comprises a unique oligonucleotide sequence configured to—preferably reversibly—bind to a complementary sequence of one of the attachment sites.

By providing or generating the oligonucleotides nanostructure backbone in a particular or predetermined manner, the position of the attachment sites for the labels relative to the oligonucleotide nanostructure backbone and/or the at least one first orientation indicator and one second orientation indicator are predetermined or known. Thus, providing a suitable or predetermined plurality of labels to attach at the corresponding attachment sites, information can be stored at the data storage device.

An oligonucleotide is, for example, a single stranded DNA or RNA molecule, that may be sequenced to determine its sequence of nucleotides. Complementary parts of oligonucleotides may hybridise or bind to each other.

The orientation indicators are configured to attach to the backbone, and may be used to visually determine the orientation of the data storage device in space.

Preferably, the nanostructure backbone comprises scaffold strands, and staple strands configured to bind to the scaffold strands at predetermined positions to fold the scaffold strand into a predetermined shape. The nanostructure backbone may be a DNA-origami. These DNA origami structures may range in size from a few nanometres into the micron range. For the fabrication of such DNA origami-based structures longer DNA molecules (scaffold strands)

are folded at precisely identified positions by so called staple strands. The DNA origami may be designed to provide a self-assembly nanostructure backbone of a particular predetermined shape. This enables an easy and reproducible synthesis and assembly of the backbone. Staple strands may be position-selectively functionalised. The positional resolution in this case is limited by the size of a nucleotide, which is in the range of a nanometre or below. This has been exploited in the prior art to generate fluorescent standards, wherein fluorescent dyes are connected to precisely located bands on the DNA origami. These standards are known as "nanoruler" and are used for the calibration of imaging systems like confocal or super resolution microscopes (e.g. STED), for example, as disclosed by US2014/0057805 A1.

The DNA origami provides a scaffold for the labels. Preferably, the DNA origami structure comprises at least one scaffold strand and multiple staple strands, wherein the staple strands are complementary to at least parts of the scaffold strand and configured to bring the scaffold strand into a predetermined conformation. In particular, the strands are oligonucleotides. This enables generating nanostructure backbones with predetermined two- or three-dimensional shapes that can self-assemble. Further, this enables the site-specific placement of attachment sites on the backbone.

The attachment sites being unique nucleic acid sequences, preferably of the staple strands. Preferably, the labels may be attached to staple strands of the nanostructure backbone at predetermined attachment sites. Since the staple strands are located at predetermined positions the positions of the attachment sites may equally be predetermined. Thus, the attachment site is a unique oligonucleotide sequence complementary to the attachment oligonucleotide portion of one label.

Preferably, the largest spatial extent of the nanostructure backbone is in a range from 10 nm to 10000 nm, preferably in a range from 0.1 µm to 5 µm. This enables a compact storage device and allows an optical readout, for example with a light microscope.

Preferably, the attachment sites are spaced apart from each other in a range from 1 nm to 2000 nm, preferably in a range from 200 nm to 1000 nm. This enables a dense arrangement of labels on the nanostructure backbone. The spacing between the attachment sites may be chosen depending on the resolving power of a readout device used to read out the labels. Preferable ranges may correspond to the lateral resolution achievable with different microscopic modalities such as for example single molecule localization microscopy (1 nm to 25 nm), structured illumination and STED microscopy (50 nm to 100 nm), high NA (numerical aperture) light microscopy (around 200 nm), and low NA light microscopy (around 500 nm). The labels may be distanced from each other such that the readout device can resolve the labels individually.

Preferably, the dye is a fluorophore. Preferably each label has fluorophore(s) with different characteristics, such as excitation/emission wavelength, to enable generating a larger number of different labels. According to a preferred embodiment, the dye is a combination of dyes as described in the patent application with the application number PCT/EP2021/073819, the complete content thereof is incorporated herein by reference.

Preferably, the nanostructure backbone extends linearly in one dimension and the first orientation indicator and the second orientation indicator are spaced apart from each other, or arranged on opposite ends of the nanostructure backbone. This enables determining the orientation of the storage device and/or of the oligonucleotide nanostructure backbone. The orientation indicators may comprise fluorescent dyes, for example. In particular, the first orientation indicator and the second orientation indicator have different properties, such as excitation wavelength, fluorescence emission wavelength, and/or fluorescence lifetime.

Preferably, the nanostructure backbone extends in two dimensions or three dimensions and the nanostructure backbone comprises at least a third orientation indicator. This enables determining the orientation of the storage device as well as providing a two-dimensional or three-dimensional storing device enabling to store additional positional information in two or three dimensions.

Preferably, the labels further comprise an encoding oligonucleotide portion configured to encode characteristics of the at least one dye. This enables reading out the storage device not only visually, but also by sequencing of at least the labels of the storage device.

Preferably, the labels comprise primer sequences configured to enable sequencing of the attachment portion and/or the encoding portion, preferably, all labels comprise the same primer sequences. This enables particular efficient sequencing of the portions.

Preferably, each label comprises a cleavage site configured to separate the dye from the label. The cleavage site may allow enzymatic, temperature, or light induced cleavage. This enables efficient removal of the dye from portions of the label, prior to sequencing the portions.

In a further aspect, a method for storing and accessing data is provided, comprising the following steps: generating or providing at least one data storage device, in particular having the characteristics as described above, including selecting a label with at least one dye based on the data to be stored at a particular one of the attachment sites and based on a predetermined set of rules, in particular, the set of rules associating the dye to a particular data; generating an optical readout of the data storage device; determining in the optical readout the at least one dye of the label for the particular one of the attachment sites; and retrieving the data based on the predetermined set of rules, in particular, the set of rules may include information about the particular one of the attachment sites.

The optical readout may be an image-based readout, in particular a 2D image or an image stack or a 3D image, which may be acquired using a microscope like a point-scanning confocal or a camera-based/widefield imaging system or for example a spinning disk microscope, a light sheet fluorescence microscope, a light field microscope, a stereomicroscope. Further the optical readout may be non-image-based readouts for example in a cytometer or a flow-through based readout device with at least one point detector or a line detector. A readout may consist of a discrete readout, for example a single acquisition of an emission spectrum or image stack, a readout may be a readout data stream, for example in a point-scanning confocal or cytometer, which is substantially continuous. Further a readout may be a sequence of images for example a spectral or hyperspectral image stack, wherein in each image fluorescence emission of different wavelength bands is recorded.

The optical readout may be generated by a readout device used to perform fluorescence multi-colour reading or imaging. The readout device typically includes at least one excitation light source, a detection system including at least one detection channel and may further contain filters and/or dispersive optical elements such as prisms and/or gratings to route excitation light to the device and/or to route emission light from the device onto one or more detectors or onto an appropriate area of a detector. The detection system may comprise several detection channels, may be a spectral detector detecting multiple bands of the spectrum in parallel, or a hyperspectral detector detecting a contiguous part of the spectrum. The detection system contains at least one detector, which may be a point-detector (e.g. a photomultiplier, an avalanche diode, a hybrid detector), an array-detector, a camera, hyperspectral camera. The detection system may record intensities per channel as is typically the case in cytometers or may be an imaging detection system that records images as in the case of plate readers or microscopes. A readout device with one detector channel, for example a camera or a photomultiplier, may generate readouts with multiple detection channels using, for example, different excitation and emission bands.

Preferably, the predetermined set of rules is stored for accessing the data and information about the particular one of the attachment sites. This enables efficient retrieval of the data from the storage device. For secure storage of data with the data storage device, the predetermined set of rules may be kept secret. Alternatively, the predetermined set of rules may be public knowledge.

In a further aspect, a plurality of labels is provided, for attaching to a plurality of attachment sites of an oligonucleotide nanostructure backbone, each label comprises at least one dye and an attachment oligonucleotide portion configured to attach the label to one of the attachment sites of the oligonucleotide nanostructure backbone, and the attachment oligonucleotide portion of each label comprises a unique oligonucleotide sequence configured to bind to a complementary sequence of one of the attachment sites of the oligonucleotide nanostructure backbone in order to generate a data storage device according to one of the preceding claims by attaching at least one of the labels to one of the attachment sites of the oligonucleotide nanostructure backbone.

In another aspect, at least one oligonucleotide nanostructure backbone is provided comprising: a plurality of attachment sites at predetermined positions and at least a first orientation indicator and a second orientation indicator, the attachment sites of the oligonucleotide nanostructure backbone are configured to attach a plurality of labels, each label comprising at least one dye and an attachment oligonucleotide portion configured to attach the label to one of the attachment sites of the oligonucleotide nanostructure backbone, and the attachment oligonucleotide portion of each label comprises a unique oligonucleotide sequence configured to bind to a complementary sequence of one of the attachment sites of the oligonucleotide nanostructure backbone in order to generate a data storage device according to one of the preceding claims by attaching at least one of the labels to one of the attachment sites of the oligonucleotide nanostructure backbone.

In a further aspect, a database is provided comprising information about the predetermined set of rules, in particular, corresponding to at least one of the following: at least one oligonucleotide nanostructure backbone; at least a first orientation indicator and a second orientation indicator of the at least one oligonucleotide nanostructure backbone; a plurality of attachment sites of the at least one oligonucleotide nanostructure backbone; predetermined positions of the plurality of attachment sites of the at least one oligonucleotide nanostructure backbone; a plurality of labels; at least one dye of each label; an attachment oligonucleotide portion of each label, in particular, being configured to attach the label to one of the attachment sites of the oligonucleotide nanostructure backbone; and which label is attached to which attachment site of the oligonucleotide nanostructure backbone.

FIG. 1 shows schematically oligonucleotide nanostructure backbones 100, 102, 104, 106, 108 with different geometries. Generally, the nanostructure backbones 100, 102, 104, 106, 108 comprise nucleic acids. In particular, the nanostructure backbones 100, 102, 104, 106, 108 are DNA-origami based, which allows generating predetermined, stable two- and three-dimensional shapes. Further, this allows generating a plurality of attachment sites at predetermined positions along the nanostructure backbones 100, 102, 104, 106, 108. The attachment sites are stretches of oligonucleotide, that are unique and allow the hybridisation of complementary oligonucleotides, for example to attach labels to the nanostructure backbones 100, 102, 104, 106, 108 at these predetermined positions.

Nanostructure backbone 100 is linear or rod-like. It comprises a first orientation indicator 110 and a second orientation indicator 112. The orientation indicators 110, 112 may be used to determine the orientation, directionality or polarity of the nanostructure backbone 100. The orientation indicators 110, 112 may comprise a dye, in particular a fluorescent dye, such as fluorescein or a fluorescent protein. In addition, the dye of the first orientation indicator 110 has different characteristics than the dye of the second orientation indicator 112. The characteristics may include fluorescent emission characteristics, excitation characteristics or lifetime characteristics. This enables differentiating between the first and the second orientation indicators 110, 112 in an optical readout of the nanostructure 100, for example generated by a microscope, a cytometer, or an imaging cytometer. The orientation indicators 110, 112 are arranged spaced apart from each other. Preferably each orientation indicator 110, 112 is arranged on the backbone 100 at opposite ends. Thus, the first and second orientation indicators 110, 112 enable differentiating between a first end and a second end of the backbone 100. Ultimately, this enables determining the orientation, directionality or polarity of the backbone 100, for example from the first orientation indicator 110 on the first end to the second orientation indicator 112 on the second end.

The nanostructure 102 is sheet-like, which may be a large linear DNA molecule or an assembly of multiple DNA molecules. Sheet-like nanostructures may increase the number of available attachment sites substantially. In order to be able to determine the orientation of the nanostructure 102, a third orientation indicator 114 is provided.

Further geometries are possible, for example, the tetrahedral nanostructure 104, the cubic nanostructure 106, or the polyhedral nanostructure 108. These may comprise a fourth orientation indicator 116 in order to determine their orientation.

Figure 2:
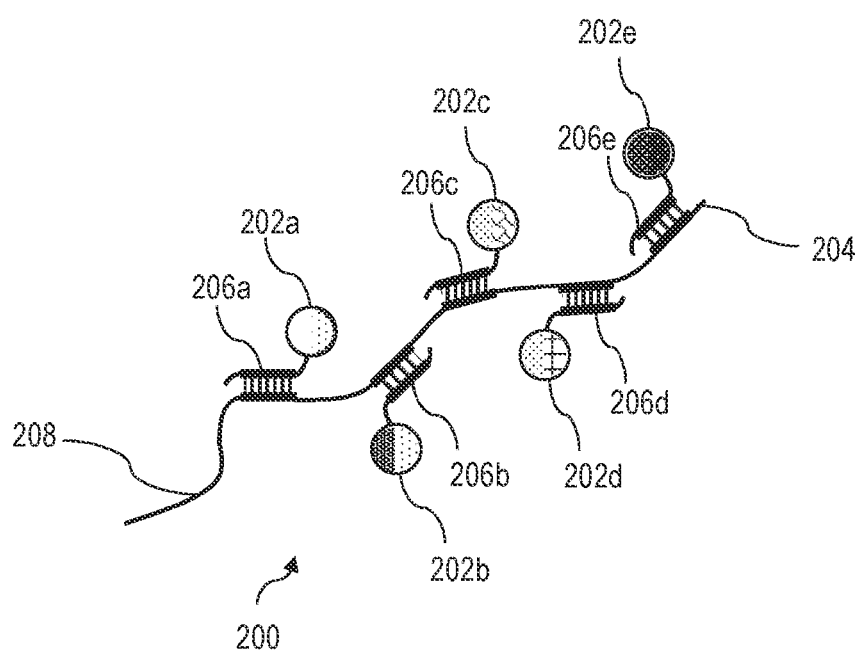
FIG. 2 shows a label for attachment to attachment sites of the nanostructure backbones according to some embodiments.

FIG. 2 shows schematically a label 200 for attachment to the attachment sites of the nanostructure backbones 100, 102, 104, 106, 108. The label 200 comprises several fluorescent dyes 202*a*, 202*b*, 202*c*, 202*d*, 202*e*. The fluorescent dyes 202*a* to 202*e* may differ in their fluorescent properties, for example, excitation wavelengths, emission wavelengths and fluorescent lifetime characteristics. Preferably, the dyes 202*a* to 202*e* of the label 200 may be individually identified in a read-out in particular of the label 200. Depending on the number and type of dyes being used when generating the label 200, a certain number of unique labels can be generated. Typically, the number of different dyes used in total may be in the range of 5-50, for example. For 20 dyes and when using 5 dyes for each label it is easily possible to generate a set of labels with 15,504 unique labels.

The dyes 202a to 202e are individually attached to a label support 204. The label support 204 may be an oligonucleotide and each of the dyes 202a to 202e may be specifically attached to the label support 204 via a unique hybridisation part 206a, 206b, 206c, 206d, 206e. Moreover, the one end 208 of the label support 204 may be specifically attached to the nanostructure backbones 100 to 108, as described in more detail below. The orientation indicators 110, 112, 114, 116, preferably have the same structure as described for the label 200. Thus, the dye can in particular be a combination of dyes as described in the patent application with the application number PCT/EP2021/073819.

Figure 3:
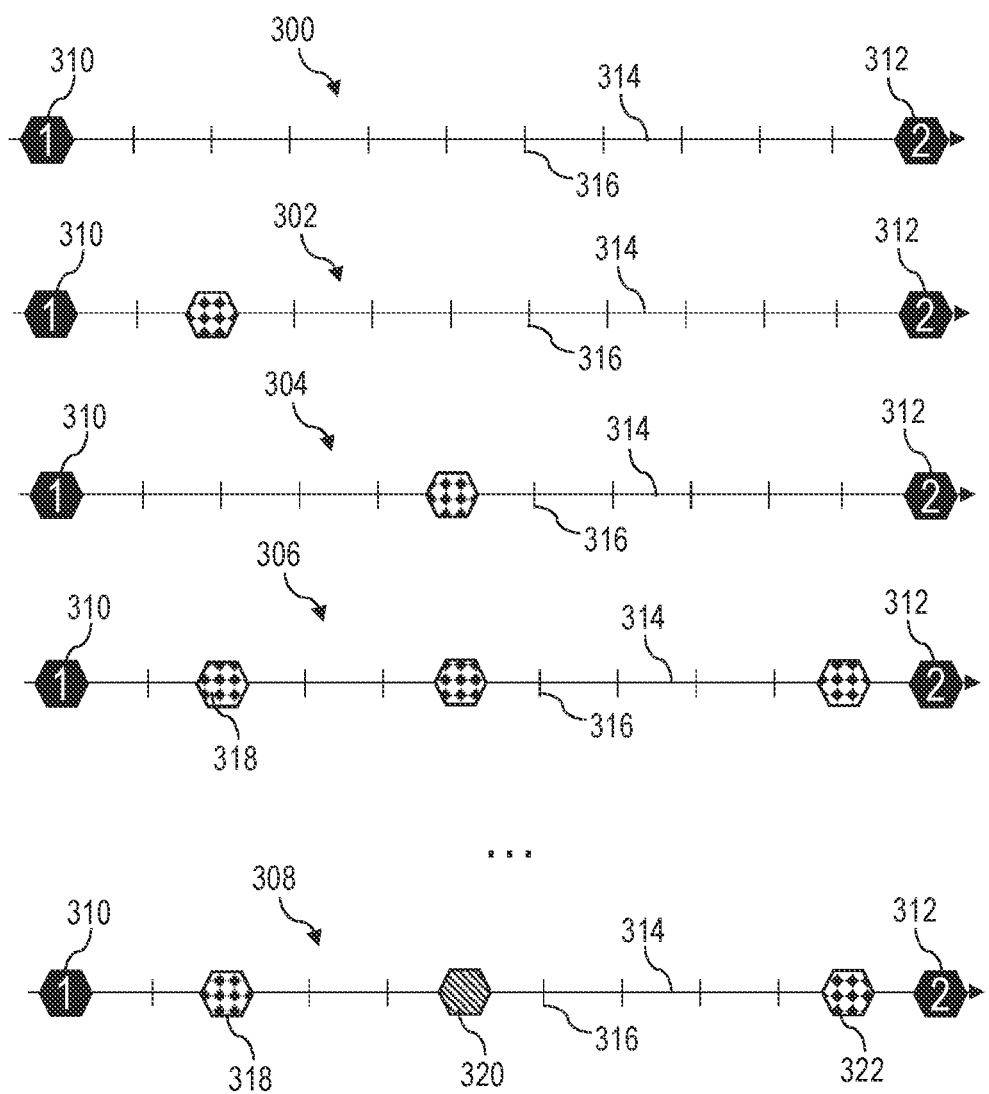
FIG. 3 shows a variety of rod-shaped data storage devices according to some embodiments.

FIG. 3 shows schematically a variety of rod-shaped data storage devices 300, 302, 304, 306, 308. The data storage devices 300 to 308 each comprise a first orientation indicator 310 and a second orientation indicator 312, at a first attachment site and a second attachment site of the nanostructure backbone 314, respectively. In addition, there are ten further attachment sites, one of which is indicated by reference sign 316. In case of the data storage devices 308, labels 318, 320, 322 are attached at three further attachment sites 316. The attachment sites 316 of each nanostructure backbone 314 is unique such that the labels 318, 320, 322 are specifically attachable to a particular attachment site 316. The data storage devices 300, 302, 304, 306, 308 are preferably between 1 to 2 µm in length.

The orientation indicators 310, 312 generate a relative coordinate system for the data storage devices 300, 302, 304, 306, 308, on which each attachment site 316 may be placed. For example, each attachment site 316 may be assigned an index n with n=1, 2, 3, . . . , based on the unique location of the respective attachment site 316. Thus, the different data storage devices 300 to 308 can all be identified and/or distinguished visually, due to their use of labels with differing properties and/or the labels being attached at different, distinguishable attachment sites 316 along the nanostructure backbone 314.

Figure 4:
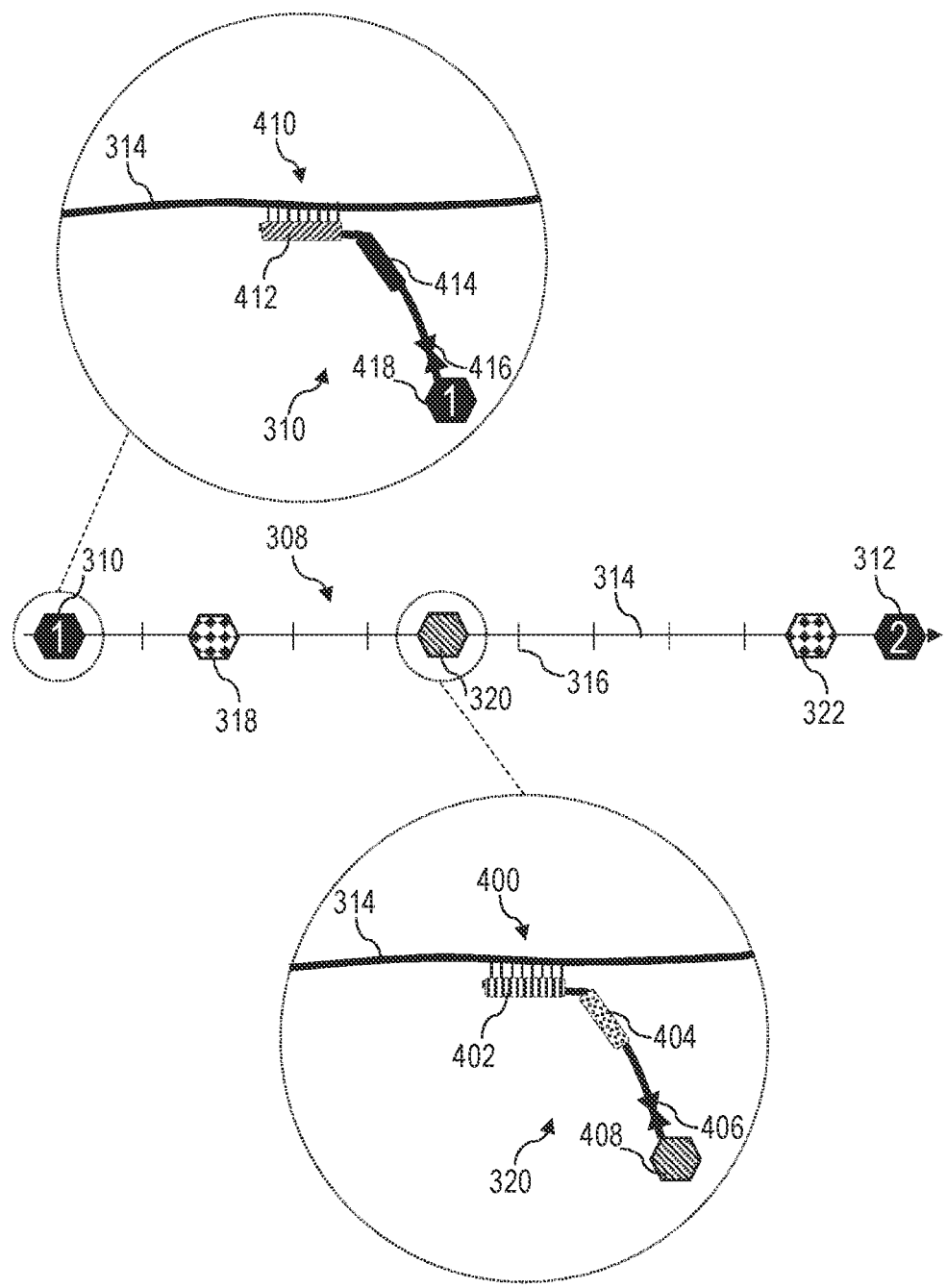
FIG. 4 shows details of a rod-shaped data storage device according to some embodiments.

FIG. 4 shows schematically details of the rod-shaped data storage device 308, in particular, the label 320 and its attachment to the nanostructure backbone 314. The label 320 is attached to the nanostructure backbone 314 at a particular attachment site 400 of the nanostructure backbone 314. This attachment site 400 has a unique oligonucleotide sequence that allows hybridisation of a complementary attachment oligonucleotide portion 402 of the label 320. Thus, each attachment site of the data storage device 308 has a unique oligonucleotide sequence enabling to specifically target labels for each one of the attachment sites. Thus, each label has a unique sequence that hybridises to a particular one of the attachment sites of a nanostructure backbone (e.g. the attachment portion 402).

Optionally in addition, the label 320 may comprise an encoding oligonucleotide portion 404. The encoding portion 404 is an oligonucleotide sequence that is unique to the fluorescent dye or dyes 408 of the label 320. This means that the dyes of a particular label may be identified by the sequence of their encoding portion. To facilitate sequencing the label 320 may also comprises a cleavage site 406 for removing the dye 408 from the encoding portion 404 and the attachment portion 402 prior to sequencing. This allows not only reading the label and the data storage device visually, but also by sequencing.

The first and second orientation indicators 310, 312 are similarly constructed. For example, the orientation indictor 310 is attached to an attachment site 410 of the nanostructure backbone 314 by a unique complementary attachment oligonucleotide portion 412.

Optionally, the orientation indictor 310 may further comprise an encoding portion 414, that is unique to the dye or dyes 418 of the orientation indicator. The dyes 418 may be removed from the encoding portion 414 and the attachment portion 412 by cleaving an optional cleavage site 416, as explained for label 320.

Figure 5:
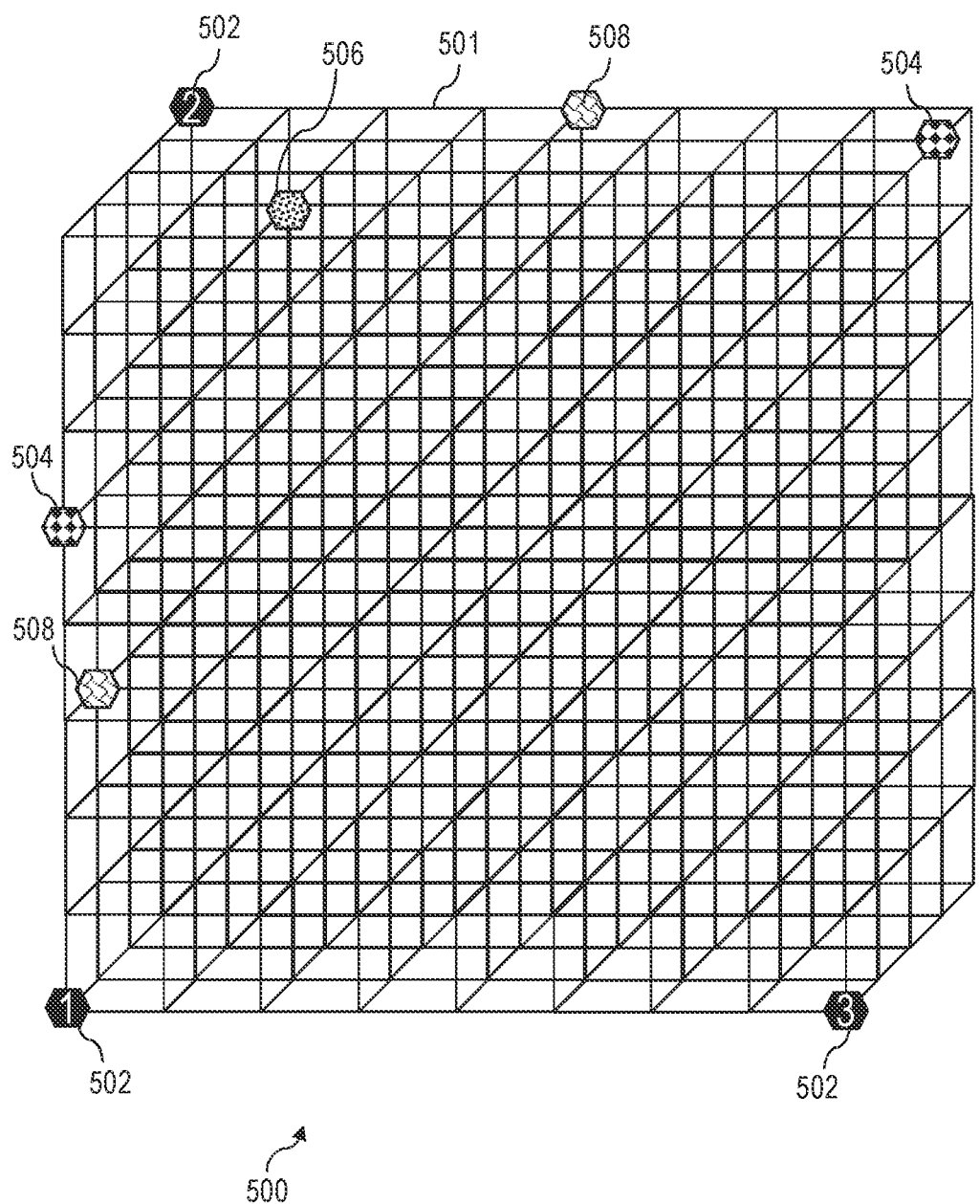
FIG. 5 shows a cube-shaped data storage device according to some embodiments.

FIG. 5 shows schematically an example of a cube-shaped data storage device 500 with a three-dimensional array nanostructure backbone 501. The data storage device 500 comprises three orientation indicators 502. Further, the data storage device 500 comprises a set of different labels 504, 506, 508. Each label 504, 506, 508 is attached at a particular attachment site of the data storage device 500. The attachment sites may, for example, be at the corners or edges of the array of the backbone 501. The labels 504, 506, 508 differ in their fluorescent properties, such as fluorescent lifetime, emission wavelength and excitation wavelength.

Thus, similarly to the data storage devices 300 to 308 in FIG. 3, the data storage device 500 may contain information in the particular placement of labels on the attachment sites of the backbone 501. This information may be readout visually. In comparison to the rod-shaped data storage devices 300 to 308, the cube-shaped data storage device 500 provides for around 360 attachment sites for labels, which increases the number of possible combinations of labels and their position on the backbone 501. This increases the possible amount of information that may be stored in the data storage device 500. A further parameter to increase storage capacity is the number of different dyes that may be used to generate the labels. By these means, a data storage density of about 1 to 5 Tbit/inch$^2$ can be achieved. A particular example of data storage with such a data storage device is explained with FIG. 6. The physical size of the cube-shaped storage device 500 is in the range of 2.5 to 10 µm per side of the cube.

Figure 6:
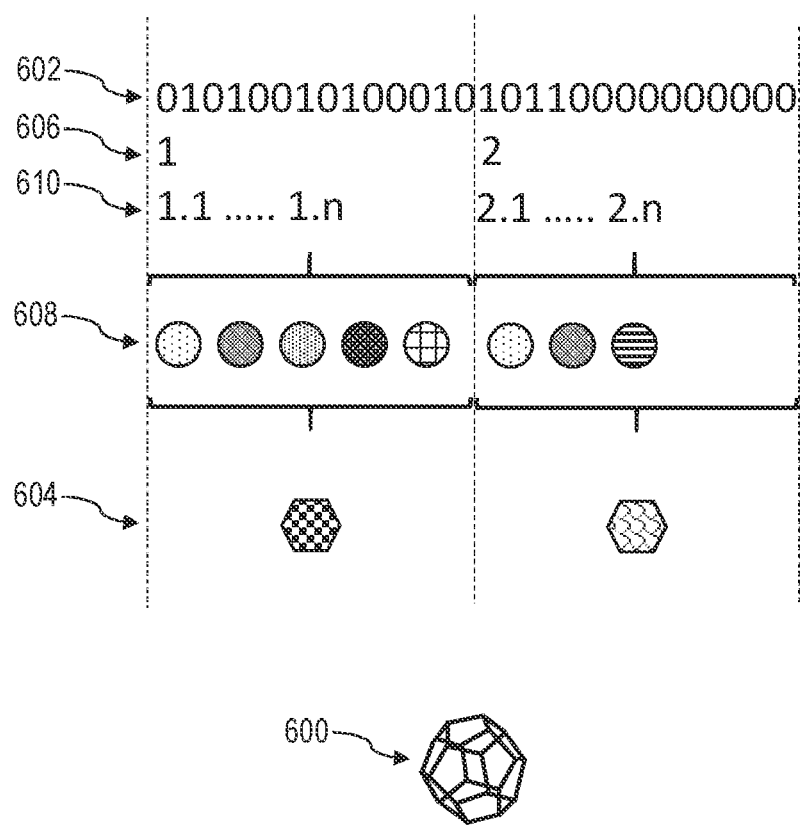
FIG. 6 shows the elements of a data storage device for storing data according to some embodiments.

FIG. 6 shows schematically how elements of a data storage device 600 may be used to store data on the data storage device and retrieve it. That data is shown in FIG. 6 as a sequence of binary data 602. The binary data 602 may be encoded in several labels 604, exemplarily in FIG. 6 two labels 604, attachable to attachment sites of a nanostructure backbone of data storage device 600. Thus, the binary data 602 is stored over several labels 604 and distributed accordingly. Each label 604 is assigned a specific attachment site 606 of the backbone of the storage device 600, that means, that each label has a particular attachment oligonucleotide sequence that enables hybridisation with that specific attachment site 606. Since each label 604 may comprise several dyes 608, each attachment site 606 or label 604 may store a corresponding amount of the data 602. For example, if 10 dyes 608 are used, each label 604 or each attachment site 606 may hold 10 bits. Thus, each dye 608 stores a particular part of the data 602. Specifically, each dye 608 has a corresponding index 610, that identifies the attachment site 606 and the particular part of the data 602 that is stored in that dye 608. For example, the index 610 of 1.1 identifies the dye 608 that encodes the first bit of data 602 at the first attachment site 606. Specific characteristics of the dyes 608, such as their fluorescent lifetime, emission/excitation wavelengths, may be defined as representing a particular state (e.g. 0 or 1) of a particular bit of the binary data 602. Alternatively, the presence of a particular dye 608 at a particular index 610 may represent a particular state (e.g. 0 or 1) of the particular bit of data 602 at the particular index 610. Alternatively or additionally, any other representation could be used. For instance, an octal, a decimal, or a hexadecimal representation, in particular depending on the number of different dyes in a combination of dyes as described in the patent application with the application number PCT/EP2021/073819. If e.g. eight different dyes are used for one combination of dyes, an octal representation of the information could be used. The higher the number of different dyes is used for one combination of dyes 604, the less attachment sites 606 are necessary in order to encode the same information. Furthermore, it might be possible to even apply different representations based on different numbers of different dyes in the combination of dyes, if the dyes 604 of e.g. an octal representation are only applied to a particular kind of oligonucleotide nanostructure backbone being identifiable by the at least first, second and/or any further orientation indicator. Moreover, since the dyes 608 may differ in more than one characteristic, the dyes 608 may represent more than two (binary) states.

In order to store the data 602 in the storage device 600, the storage device 600 has to be generated based on the data 602 to be saved and based on a set of rules. The set of rules may be predetermined before generation of the device 600 and comprises the information discussed in the above paragraph. Specifically, at least the following information is needed for storing the data 602: the layout of the nanostructure backbone of the device 600, in particular the numbering of the attachment sites 606 on the backbone or in other words the sequence of attachment sites 606 in which the data is encoded, the assignment of a particular dye 608 or characteristic of the dye 608 to a state (e.g. 0 or 1), and which dye 608 of a label 604 corresponds to which bit of the data 602 at a particular attachment site 606 (this being encoded in the index 610). Subsets of this information may be used as private keys and public keys, for example, for asymmetric cryptography. Alternatively, both keys may be held private.

Figure 7:
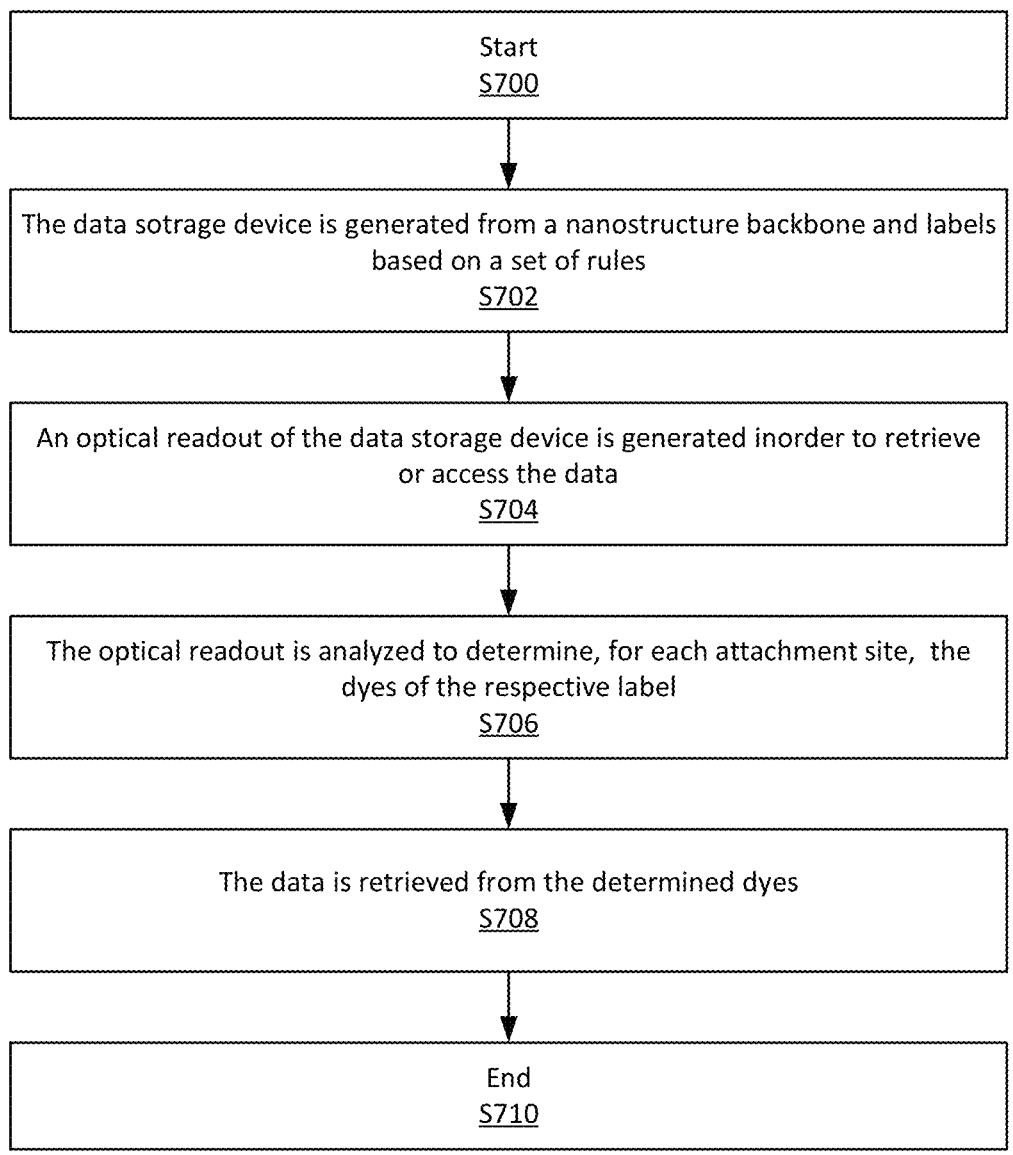
FIG. 7 shows a flow chart of a method for storing and retrieving data according to some embodiments.

FIG. 7 shows a flow chart of a method for storing and accessing the data 602 in the storage device 600. The method starts in step S700. In a first step S702, the data storage device 600 is generated from a nanostructure backbone and labels based on a set of rules described with FIG. 6. This stores the data 602 in the device 600.

In step S704, an optical readout of the device 600 is generated in order to retrieve or access the data 602 stored in the device 600.

Alternatively, in case the device comprises encoding oligonucleotide portions, as described above, the dyes of a particular label may be identified by the sequence of their encoding portion. This means that in this case, the device may be readout by sequencing the device.

In step S706, the optical readout generated in step S704 is analysed to determine for each attachment site 606 the dyes 608 of the respective labels 604.

In step S708, the data 602 is retrieved from the information determined in step S706 based on the set of rules used in step S702. To that end, the set of rules may be stored, in order to facilitate data retrieval, and/or the set of rules may be kept secret, in order to secure the data 602 stored in the device 600. The method ends in step S710.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS 100, 102, 104, 106, 108, 314, 501 Nanostructure backbone
110, 112, 114, 310, 312, 502 Orientation indicator
200, 318, 320, 322, 504, 506,
508, 604 Label
202a, 202b, 202c, 202d, 202e,
408, 418, 608 Fluorescent dye
204 Label support
206a, 206b, 206c, 206d, 206e Hybridisation part
208 End of label support
406, 416 Cleavage site
300, 302, 304, 306, 308, 500, 600 Data storage device
316, 400, 410, 606 Attachment site
402, 412 Attachment oligonucleotide portion
404, 414 Encoding oligonucleotide portion
602 Binary data
610 Index

The invention claimed is:
1. A data storage device comprising:
an oligonucleotide nanostructure backbone with a plurality of attachment sites at predetermined positions,
a plurality of labels, each respective label to be attached to a respective attachment site of the plurality of attachment sites, each respective label comprising:
at least one dye for encoding respective binary data,
an attachment oligonucleotide portion comprising a respective oligonucleotide sequence configured to bind to a complementary sequence of the respective attachment site, and
an encoding oligonucleotide portion comprising a respective oligonucleotide sequence that is unique to the at least one dye, the encoding oligonucleotide portion facilitating identifying the respective label, and at least a first orientation indicator and a second orientation indicator attached to the oligonucleotide nanostructure backbone for visually determining an orientation of the data storage device.

2. The data storage device according to claim 1, wherein the oligonucleotide nanostructure backbone comprises scaffold strands, and staple strands configured to bind to the scaffold strands at the predetermined positions to fold the scaffold strands into a predetermined shape.

3. The data storage device according to claim 2, wherein the staple strands comprise the attachment sites.

4. The data storage device according to claim 1, wherein a largest spatial extent of the oligonucleotide nanostructure backbone is in a range from 10 nm to 10000 nm.

5. The data storage device according to claim 1, wherein the attachment sites are spaced apart from each other with a spacing in a range from 1 nm to 2000 nm.

6. The data storage device according to claim 1, wherein the at least one dye is a fluorophore.

7. The data storage device according to claim 1, wherein the oligonucleotide nanostructure backbone extends linearly in one dimension, and the first orientation indicator and the second orientation indicator are spaced apart from each other, or arranged on opposite ends of the oligonucleotide nanostructure backbone.

8. The data storage device according to claim 1, wherein the oligonucleotide nanostructure backbone extends in two dimensions or three dimensions, and the oligonucleotide nanostructure backbone comprises at least a third orientation indicator.

9. The data storage device according to claim 1, wherein the labels comprise primer sequences configured to enable sequencing of at least the encoding oligonucleotide portion.

10. The data storage device according to claim 9, wherein all the labels comprise same primer sequences.

11. A method for storing and accessing data, the method comprising:

providing an oligonucleotide nanostructure backbone comprising a plurality of attachment sites at predetermined positions, and at least a first orientation indicator and a second orientation indicator for visually determining an orientation of the oligonucleotide nanostructure backbone, selecting a plurality of labels based on the data to be stored and based on a predetermined set of rules, each respective label comprising:

at least one dye for encoding respective binary data, an attachment oligonucleotide portion comprising a respective oligonucleotide sequence configured to bind to a complementary sequence of a respective attachment site, and an encoding oligonucleotide portion comprising a respective oligonucleotide sequence that is unique to the at least one dye, attaching the plurality of labels to the oligonucleotide nanostructure backbone, each respective label being attached to a respective attachment site of the plurality of attachment sites, generating an optical readout of the plurality of labels attached to the oligonucleotide nanostructure backbone, determining in the optical readout the at least one dye of each respective label for the respective attachment site of the plurality of attachment sites, and retrieving the data based on the predetermined set of rules.

* * * * *